(12) United States Patent
Hitzke et al.

(10) Patent No.: US 7,792,245 B2
(45) Date of Patent: Sep. 7, 2010

(54) BREAST TOMOSYNTHESIS SYSTEM WITH SHIFTING FACE SHIELD

(75) Inventors: Georgia Hitzke, Boston, MA (US);
Kathleen Pickett, Uncasville, CT (US);
Nikolaos Gkanatsios, Danbury, CT (US); Ken Defreitas, Patterson, NY (US); Tom Farbizio, Patterson, NY (US); John Girgenti, New Milford, CT (US); Tim Stango, Sandy Hook, CT (US)

(73) Assignee: Hologic, Inc., Bedford, MA (US)

( * ) Notice: Subject to any disclaimer, the term of this patent is extended or adjusted under 35 U.S.C. 154(b) by 0 days.

(21) Appl. No.: 12/491,147

(22) Filed: Jun. 24, 2009

(65) Prior Publication Data
US 2009/0323892 A1    Dec. 31, 2009

Related U.S. Application Data

(60) Provisional application No. 61/075,226, filed on Jun. 24, 2008.

(51) Int. Cl.
*A61B 6/03* (2006.01)
*H01J 35/16* (2006.01)

(52) U.S. Cl. ......................................... 378/37; 378/203

(58) Field of Classification Search ................... 378/37, 378/62, 64, 68, 70, 95, 97, 197, 203, 207, 378/208
See application file for complete search history.

(56) References Cited

U.S. PATENT DOCUMENTS

| | | | |
|---|---|---|---|
| 3,502,878 A | 3/1970 | Stewart | |
| 3,863,073 A | 1/1975 | Wagner | |
| 3,971,950 A | 7/1976 | Evans et al. | |
| 4,160,906 A | 7/1979 | Daniels et al. | |
| 4,559,641 A | 12/1985 | Caugant et al. | |
| 4,744,099 A | 5/1988 | Huettenrauch et al. | |
| 4,773,086 A | 9/1988 | Fujita et al. | |
| 4,821,727 A | 4/1989 | Levene et al. | |
| 4,969,174 A | 11/1990 | Scheid et al. | |
| 4,989,227 A | 1/1991 | Tirelli et al. | |

(Continued)

FOREIGN PATENT DOCUMENTS

EP    0775467 A1    5/1997

(Continued)

OTHER PUBLICATIONS

Heang-Ping Chan et al., "ROC study of the effect of stereoscopic imaging on assessment of breast lesions", Medical Physics, vol. 32, No. 4, Apr. 2005.

(Continued)

*Primary Examiner*—Irakli Kiknadze
(74) *Attorney, Agent, or Firm*—Cooper & Dunham LLP

(57) ABSTRACT

Breast imaging using any one of a mammography system, a tomosynthesis system, or a fused system that selectively takes either or both of mammography images and tomosynthesis images, further uses a patient shield that moves closer to and further away from the patient's chest and head, between (1) an access position that facilitates the technologist's access to adjust the patient's breast while the breast is being compressed and (2) a protective position in which the shield helps protect the patient from collision with moving components and from x-ray exposure of tissue other than the tissue that is to be imaged.

30 Claims, 14 Drawing Sheets

U.S. PATENT DOCUMENTS

| | | |
|---|---|---|
| 5,018,176 A | 5/1991 | Romeas et al. |
| RE33,634 E | 7/1991 | Yanaki |
| 5,029,193 A | 7/1991 | Saffer |
| 5,078,142 A | 1/1992 | Siczek et al. |
| 5,163,075 A | 11/1992 | Lubinsky et al. |
| 5,164,976 A | 11/1992 | Scheid et al. |
| 5,199,056 A | 3/1993 | Darrah |
| 5,240,011 A | 8/1993 | Assa |
| 5,289,520 A | 2/1994 | Pellegrino et al. |
| 5,365,562 A | 11/1994 | Toker |
| 5,415,169 A | 5/1995 | Siczek et al. |
| 5,426,685 A | 6/1995 | Pellegrino et al. |
| 5,452,367 A | 9/1995 | Bick et al. |
| 5,506,877 A | 4/1996 | Niklason et al. |
| 5,526,394 A | 6/1996 | Siczek et al. |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzke et al. |
| 5,609,152 A | 3/1997 | Pellegrino et al. |
| 5,627,869 A | 5/1997 | Andrew et al. |
| 5,668,889 A | 9/1997 | Hara |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,872,828 A | 2/1999 | Niklason et al. |
| 5,878,104 A | 3/1999 | Ploetz |
| 5,896,437 A | 4/1999 | Ploetz |
| 5,986,662 A | 11/1999 | Argiro et al. |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers et al. |
| 6,137,527 A | 10/2000 | Abdel-Malek et al. |
| 6,141,398 A | 10/2000 | He et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,256,370 B1 | 7/2001 | Yavuz |
| 6,272,207 B1 | 8/2001 | Tang |
| 6,292,530 B1 | 9/2001 | Yavus et al. |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,411,836 B1 | 6/2002 | Patel et al. |
| 6,415,015 B2 | 7/2002 | Nicolas et al. |
| 6,442,288 B1 | 8/2002 | Haerer et al. |
| 6,459,925 B1 | 10/2002 | Nields |
| 6,556,655 B1 | 4/2003 | Chichereau et al. |
| 6,597,762 B1 | 7/2003 | Ferrant et al. |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,744,848 B2 | 6/2004 | Stanton et al. |
| 6,748,044 B2 | 6/2004 | Sabol |
| 6,751,285 B2 | 6/2004 | Eberhard |
| 6,758,824 B1 | 7/2004 | Miller et al. |
| 6,813,334 B2 | 11/2004 | Koppe et al. |
| 6,882,700 B2 | 4/2005 | Wang et al. |
| 6,885,724 B2 | 4/2005 | Li et al. |
| 6,912,319 B1 | 6/2005 | Eberhard et al. |
| 6,940,943 B2 | 9/2005 | Claus et al. |
| 6,978,040 B2 | 12/2005 | Berestov |
| 6,999,554 B2 | 2/2006 | Mertelmeier |
| 7,110,490 B2 | 9/2006 | Eberhand |
| 7,123,684 B2 | 10/2006 | Jing |
| 7,127,091 B2 | 10/2006 | Op De Beek |
| 7,245,694 B2 | 7/2007 | Jing |
| 7,315,607 B2 | 1/2008 | Ramsauer |
| 7,319,735 B2 | 1/2008 | Defreitas |
| 7,323,692 B2 | 1/2008 | Rowlands et al. |
| 7,430,272 B2 | 9/2008 | Jing et al. |
| 7,440,539 B2 * | 10/2008 | Danielsson et al. ............ 378/37 |
| 7,443,949 B2 | 10/2008 | Defreitas et al. |
| 7,492,858 B2 * | 2/2009 | Partain et al. ................. 378/37 |
| 2001/0038681 A1 | 11/2001 | Stanton et al. |
| 2002/0012450 A1 | 1/2002 | Tsujii |
| 2002/0050986 A1 | 5/2002 | Inoue et al. |
| 2003/0018272 A1 | 1/2003 | Treado et al. |
| 2003/0073895 A1 | 4/2003 | Nields et al. |
| 2003/0095624 A1 | 5/2003 | Eberhand |
| 2003/0194050 A1 | 10/2003 | Eberhand |
| 2003/0194051 A1 | 10/2003 | Wang |
| 2003/0194121 A1 | 10/2003 | Eberhard et al. |
| 2003/0209672 A1 * | 11/2003 | Nelson et al. ................. 250/394 |
| 2003/0210254 A1 | 11/2003 | Doan et al. |
| 2003/0215120 A1 | 11/2003 | Uppaluri et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0063509 A1 | 3/2005 | DeFreitas et al. |
| 2005/0078797 A1 | 4/2005 | Danielsson et al. |
| 2005/0113681 A1 | 5/2005 | Defreitas |
| 2005/0113715 A1 | 5/2005 | Schwindt et al. |
| 2005/0135555 A1 | 6/2005 | Claus et al. |
| 2005/0135664 A1 | 6/2005 | Kaufhold et al. |
| 2005/0226375 A1 | 10/2005 | Eberhard et al. |
| 2006/0030784 A1 | 2/2006 | Miller et al. |
| 2006/0098855 A1 | 5/2006 | Gkanatsios |
| 2006/0129062 A1 | 6/2006 | Nicoson et al. |
| 2006/0155209 A1 | 7/2006 | Miller et al. |
| 2006/0291618 A1 | 12/2006 | Eberhard et al. |
| 2007/0030949 A1 | 2/2007 | Jing et al. |
| 2007/0036265 A1 * | 2/2007 | Jing et al. ..................... 378/37 |
| 2007/0223651 A1 | 9/2007 | Wagenaar et al. |
| 2007/0225600 A1 | 9/2007 | Weibrecht |
| 2007/0242800 A1 | 10/2007 | Jing |
| 2008/0019581 A1 | 1/2008 | Gkanatsios |
| 2008/0045833 A1 | 2/2008 | Defreitas et al. |
| 2008/0130979 A1 | 6/2008 | Ren et al. |
| 2009/0003519 A1 | 1/2009 | Defreitas et al. |

FOREIGN PATENT DOCUMENTS

| | | |
|---|---|---|
| EP | 09820001 A1 | 3/2000 |
| EP | 1428473 A2 | 6/2004 |
| WO | WO90/05485 | 5/1990 |
| WO | WO98/16903 | 4/1998 |
| WO | WO 00/51484 | 9/2000 |
| WO | WO2005/051197 A1 | 6/2005 |
| WO | WO2005/110230 A1 | 11/2005 |
| WO | WO2005/112767 A1 | 12/2005 |
| WO | WO2006/055830 A2 | 5/2006 |
| WO | WO2006/058160 A2 | 6/2006 |

OTHER PUBLICATIONS

Federica Pediconi et al., "Color-coded automated signal intensity-curve for detection and characterization of breast lesions: Preliminary evaluation of a new software for MR-based breast imaging", International Congress Series 1281 (2005) 1081-1086.

Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle.

"Filtered Back Projection," (NYGREN) published May 8, 2007; URL: http://web.archive.org/web/19991010131715/http://www.owlnet.rice.edu/~elec539/Projects97/cult/node2.1.

Kita et al., "Correspondence between different view breast X-rays using simulation of breast deformation", Proceedings 1998 IEE Computer Society Conference on Computer Vision and Pattern Recongnition, Santa Basbara, CA, Jun. 23-25, 1998, pp. 700-707.

* cited by examiner

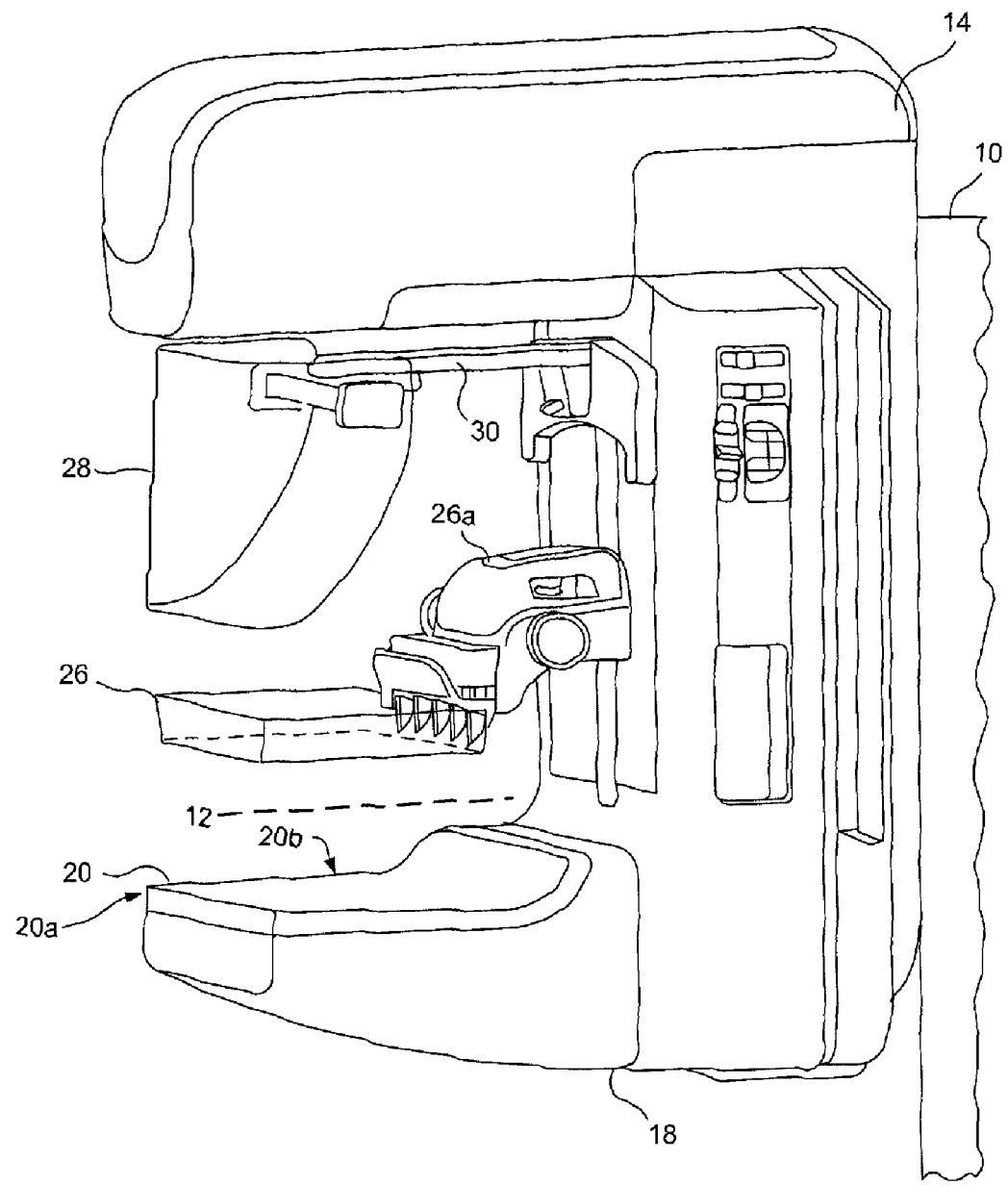
F I G. 1

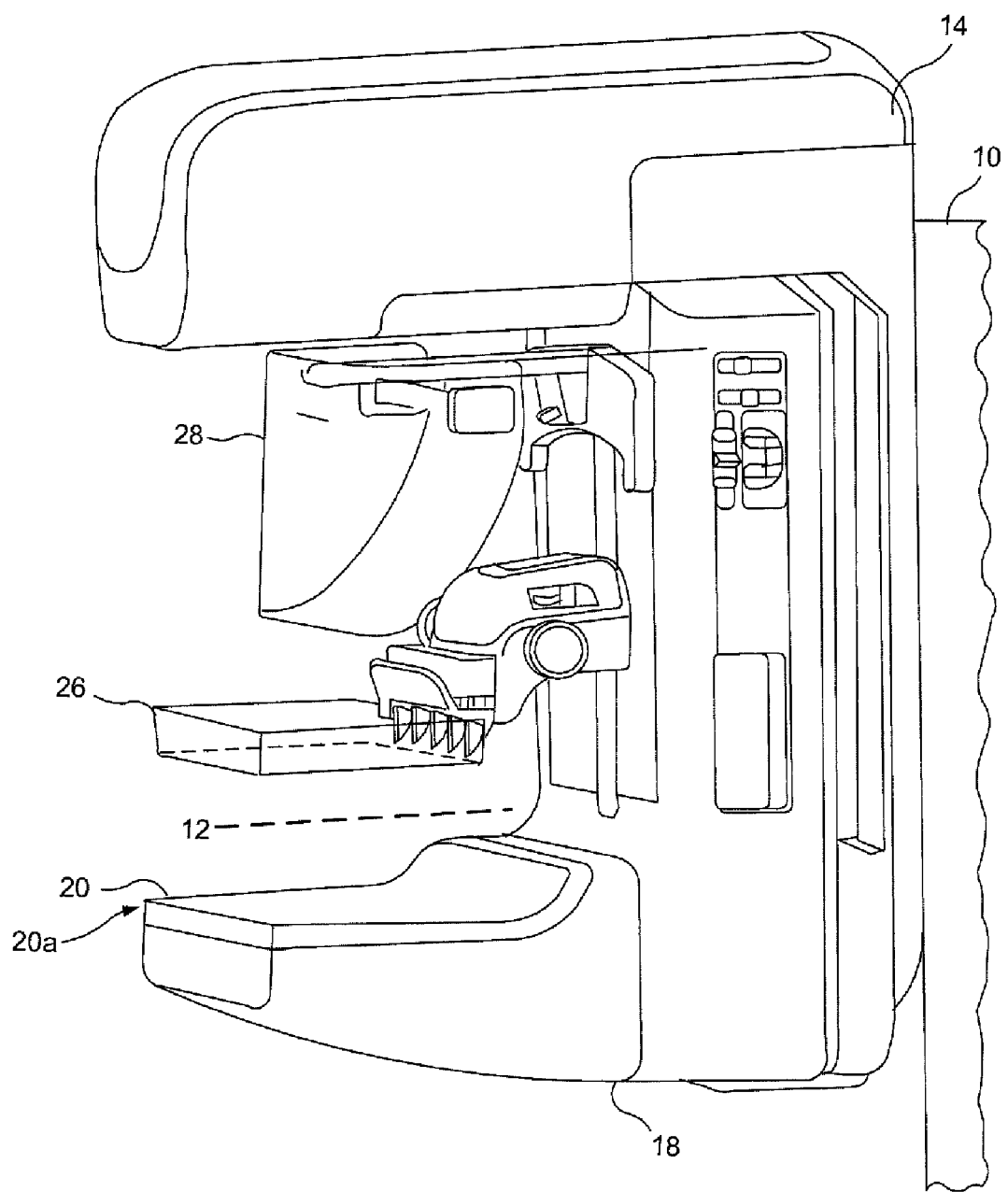
F I G. 2

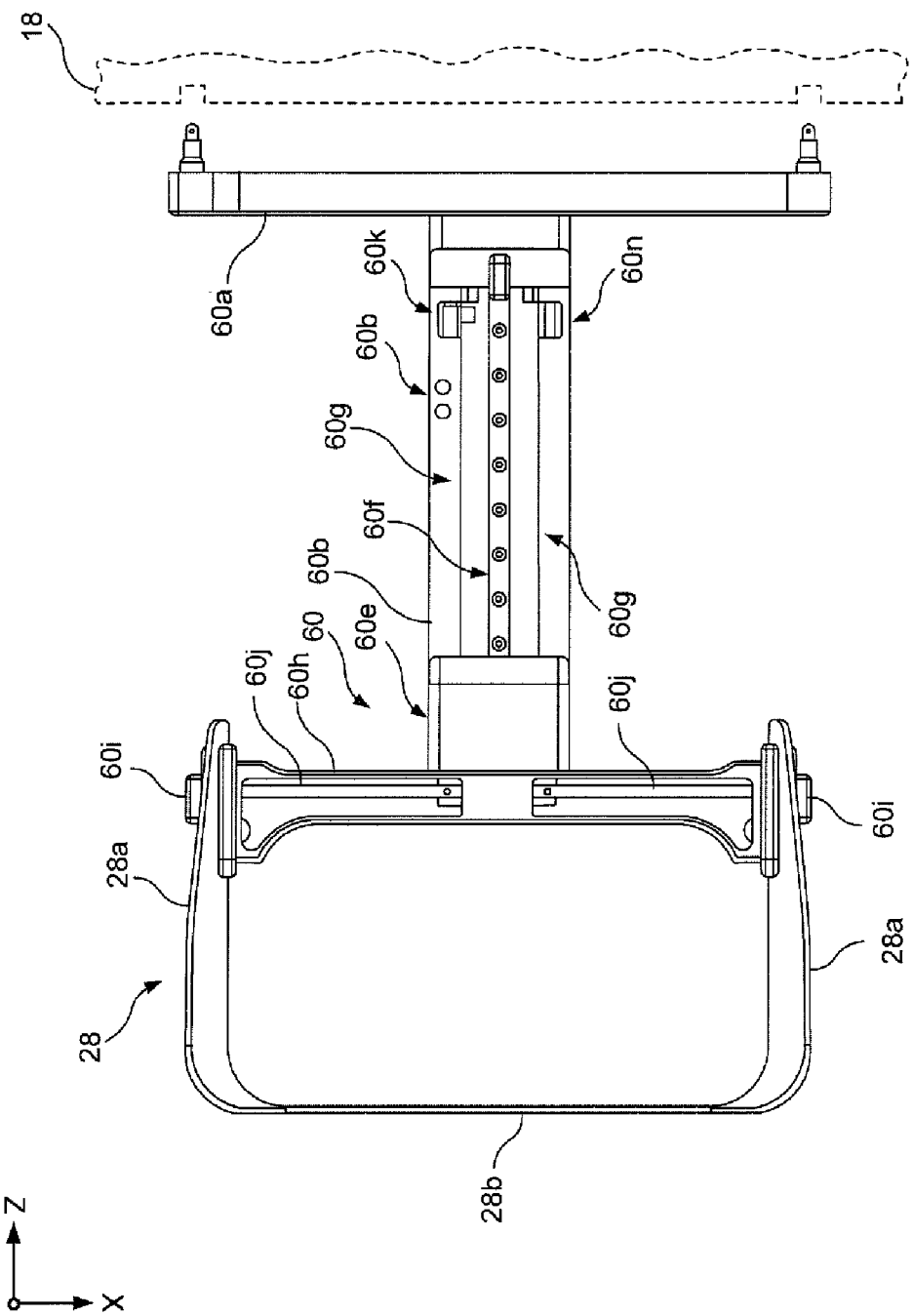
F I G. 6b

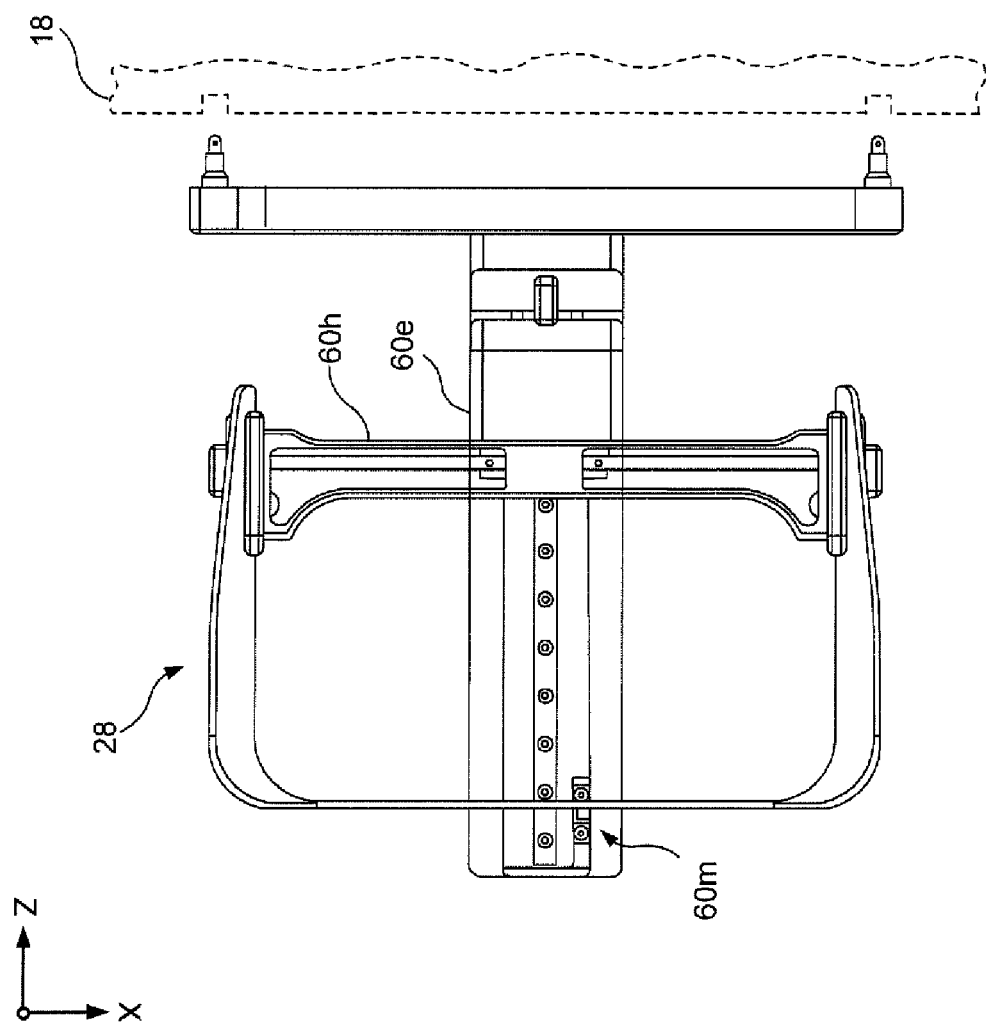

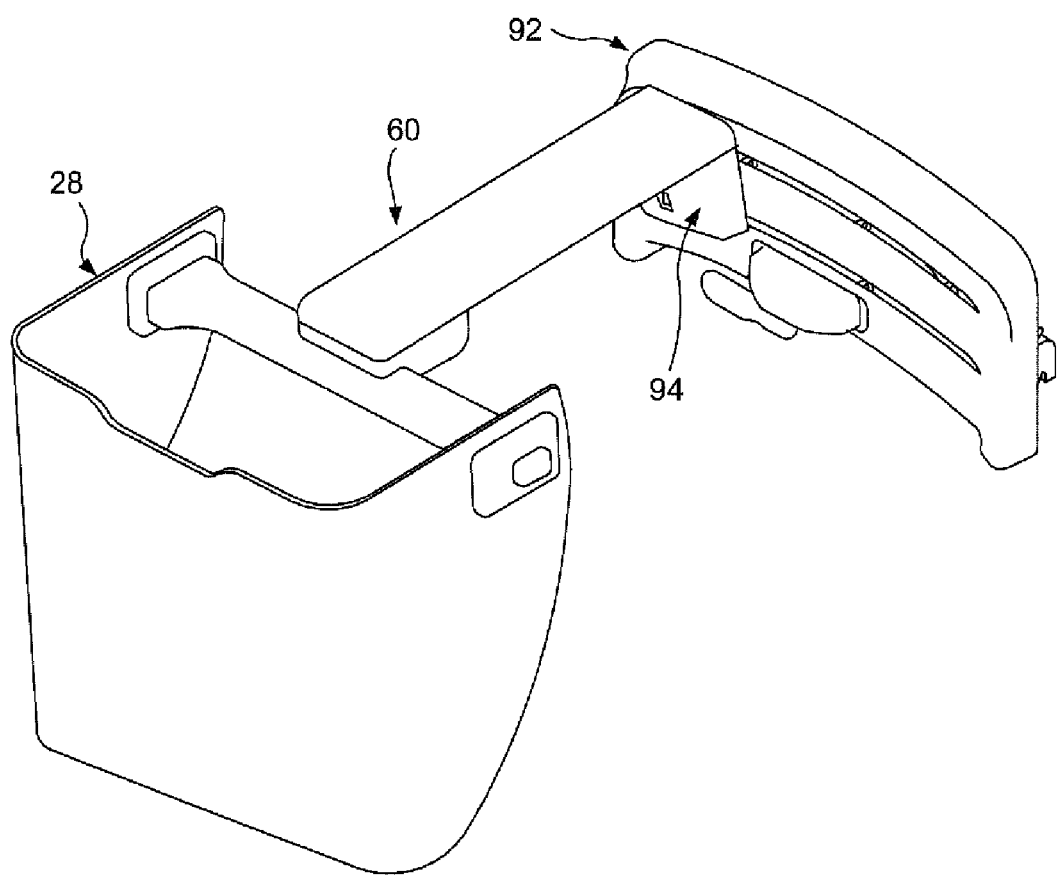
F I G. 12

BREAST TOMOSYNTHESIS SYSTEM WITH SHIFTING FACE SHIELD

CROSS-REFERENCE TO RELATED APPLICATIONS

This application claims priority benefits based on provisional application 61/075,226 filed Jun. 24, 2008 and incorporates by reference the contents of said provisional application.

TECHNICAL FIELD

This application relates to medical imaging and more specifically to x-ray imaging such as mammography and/or breast tomosynthesis and to shielding the patient from moving components of the imaging system.

BACKGROUND

In breast tomosynthesis as well as in conventional mammography and in fusion systems that can selectively carry out either or both types of imaging, a source support arm carries an x-ray source and rotates or otherwise moves from one imaging position to another. In tomosynthesis, the patient's breast remains immobilized while the x-ray source moves to allow taking a number of projection x-ray images at respective angles of the x-ray beam to the breast. The x-ray imaging receptor may or may not move in this process, depending on the design of the system. The projection x-ray images are computer-processed to reconstruct values for voxels (volume elements) that are in a three-dimensional arrangement in the breast. The set of voxel values is further computer-processed to derive tomosynthesis slice images, each representing a respective slice of the breast that has a selected orientation and a selected thickness that typically is made up of several voxels. In conventional mammography, typically only one x-ray image is taken while the patient's breast remains immobilized but another image may be taken after releasing the breast, rotating the x-ray source and the imaging x-ray receptor to a new angle relative to the breast and again immobilizing the breast. For example, in screening mammography in this country, typically two images are taken of each breast, a CC image and an MLO image. In addition, a scout shot may be taken before the imaging shots, to help select appropriate AEC (Automatic Exposure Control) settings. In a fusion system, a conventional mammogram may be taken in addition to projection tomosynthesis x-ray images while the breast remains immobilized. Alternatively, a fusion system may be used to take only one or more conventional mammography images of a breast or to take only tomosynthesis x-ray projection images (each of which requires a much lower x-ray dose than a conventional mammography x-ray image).

A number of conflicting requirements and challenges need to be addressed in the design and operation of breast x-ray image system. One is to promote image quality and patient flow. Another is to ensure patient comfort with moving system components, which means not only preventing collisions with moving components but also providing the patient with psychological comfort against concern with components that move close to the patient's body and particularly the patient's head. Yet another is to guard against the possibility that the patient's hands, arms or head may enter the x-ray field at inappropriate times. Still another is to provide the x-ray technologist with convenient and effective access to the patient's breast and chest wall tissue before and while the breast is being compressed between a breast platform and a compression paddle. The technologist's work in this respect is vital, both to the reduce patient's discomfort and to ensure image quality, because typically it is necessary to pull patient tissue away from the chest wall and into the x-ray field and also to make sure that the compressed breast is as uniform in thickness as practical, for reasons such as reducing overlap of tissue of interest along the direction of the x-ray beam, reducing scatter of x-ray during passage through the breast, and making the overall density of the image more uniform.

Patient shields have been used in an effort to meet some of these and other concerns in breast imaging. For example, commonly assigned U.S. Pat. No. 7,245,694 describes a fused mammography/tomosynthesis system that takes tomosynthesis projection x-ray images while the x-ray source moves through a trajectory that is generally to one side of the patient's head rather than symmetrically to both sides. A patient shield separates the patient's head from the x-ray source trajectory and moves to one position when the trajectory is to the right of the patient's head and to another position when the source trajectory is to the left of the patient's head. This improves over earlier proposals for shields that do not move relative to the x-ray source. U.S. Pat. No. 7,315,607 proposes a face shield that retracts up into the x-ray emitter head or extends down from the head for imaging. This is said to improve over prior art shields that were manually slipped over the x-ray emitter to prevent the patient's head from entering the x-ray beam path, and to have allowed the use of different shields for different examinations. However, it is not practical for tomosynthesis, as the shield that is attached to the x-ray emitter head would have to move as the x-ray source moves to different positions relative to the patient during tomosynthesis imaging. U.S. Pat. No. 6,999,554 proposes a shield behind which the x-ray source would rotate. Published patent application US2005/0078797 A1 proposes yet another shield. The patents and other publications identified above and below in this patent specification are hereby incorporated by reference herein.

SUMMARY OF THE DISCLOSURE

A mammography, tomosynthesis, or fused mammography/tomosynthesis system is provided with a patient shield that moves toward and away from the patient in a generally horizontal direction. In an access position, the shield is away from the patient's chest and head to allow the x-ray technologist to easily reach and manually position and adjust the patient's breast while compressing the breast prior to x-ray imaging. In a protective position, the shield is closer to the patient's chest and head and protect the patient, both physically and psychologically, from moving components such as the x-ray tube in tomosynthesis imaging. In at least the protective position, and preferably in the access position as well, the shield and its support structure are out of the imaging x-ray beam. Interlocks prevent x-ray exposure in intermediate positions of the patient shield, and can allow imaging either only when the patient shield is in its protective position or only when the shield is in one of its protective and access positions, or in each of the protective and access positions, but not in intermediate positions. The patient shield motion between its positions can be manual or motorized. The shield and its supporting structure can be secured in position through a locking mechanism that allows removal for imaging without using the shield.

BRIEF DESCRIPTION OF THE DRAWING

The subject matter of this patent specification may be more readily understood from the following detailed description with reference to the accompanying drawing in which:

FIG. 1 is a partial perspective view of a mammography and/or breast tomosynthesis system with a patient shield extended into a protective position.

FIG. 2 is similar view with the patient shield retracted into an access position.

FIGS. 6b and 7b are bottom views of the implementation seen in FIGS. 6a and 6b, respectively.

FIG. 8 is a cross-sectional view of the implementation seen in FIG. 6a.

FIGS. 9-14 illustrate another currently preferred implementation, in which a patient shield is movable both side-to-side and back-and-forth relative to an x-ray source and an x-ray imaging receptor.

DETAILED DESCRIPTION OF PREFERRED EMBODIMENTS

Figure 3:
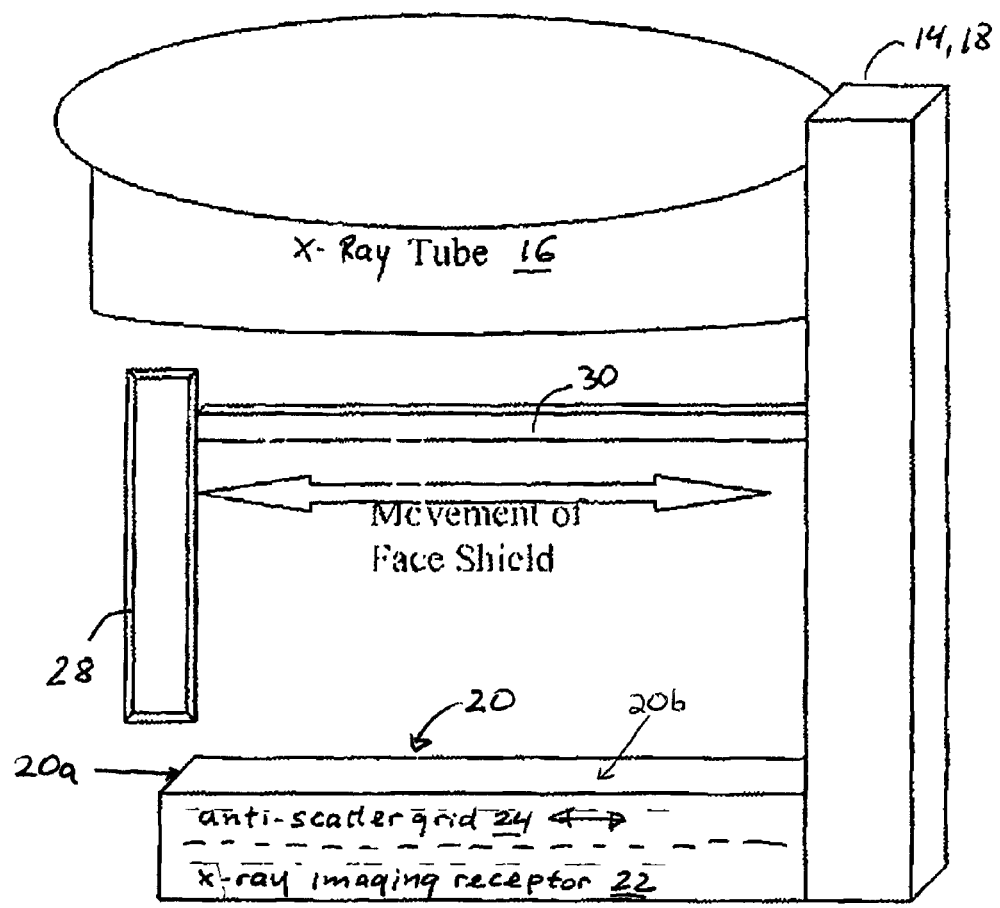
FIG. 3 is a conceptual side view of a portion of the system illustrating a motion of the shield.

In describing preferred embodiments illustrated in the drawing, this patent specification employs specific terminology for the sake of clarity but the disclosure herein is not intended to be limited to the selected terminology and it should be understood that the specific elements denoted by such terminology are intended to include all technical equivalents that operate in comparable manner. In addition, a detailed description of known functions and configurations may be omitted for the sake of conciseness or where it may obscure the subject matter that this patent specification contributes.

Referring to FIGS. 1-3, an embodiment serving as an illustrative example comprises a system that can be any one of a mammography system, a breast tomosynthesis system, and a fused mammography/tomosynthesis system, for example in the systems available or shown at trade shows in this country from the common assignee, Hologic, Inc., under the tradenames Selenia™, Selenia Dimension™ and Gemini™. Such systems are described in commonly owned U.S. Pat. Nos. 7,443,949, 7,123,684, 7,430,272, 7,319,735, US2005/0113681 A1, US2006/0098855 A1, US2008/0130979 A1, US2008/0045833 A1, US2009/0003519 A1 and US2008/0019581 A1.

The system illustrated in FIGS. 1-3 comprises a support column 10 that supports for rotation about a rotation axis 12 a first support arm 14, which is an x-ray source support arm shaped as an inverted "L" that houses in its upper portion an x-ray source 16. Support column 10 also supports for rotation about the same rotation axis 12 a second support arm 18, which is an L-shaped x-ray receptor support arm that carries, at its lower portion, a breast platform 20 and encloses an x-ray imaging receptor 22 and a movable anti-scatter grid 24. Breast platform 20 has a front edge 20a, against which the patient's chest wall presses when the patient's breast is x-ray imaged and a back end 20b. A compression paddle 26 is removably secured to a support 26a that rides up and down the vertical part of x-ray receptor arm 18 as seen in FIGS. 1 and 2. A patient shield 28 is secured to a shield support arm 30 that can move in the direction of its length into and out of receptor support arm 18 or can allow shield 28 to move toward and away from arm 18. Except for patient shield 28, shield support arm 30 and other components associated with patient shield 28 and its movement, the equipment of FIGS. 1 and 2 can be similar to the Selenia™ mammography system offered in this country by the common assignee, Hologic, Inc. of Bedford, Mass. or to the Selenia Dimension™ and Gemini™ fused breast imaging systems that have been shown by the common assignee at trade shows in this country, See Lorad Selenia™" Document B-BI-SEO US/Intl (5/06) copyright Hologic 2006, and Casey, Brian-Hologic Edges DBT mammo system to market in Europe (3/08). In the case of the Selenia™ system, x-ray source 16 and x-ray receptor arm 18 are carried on a common C-arm and remain fixed with respect to each other while the C-arm rotates to a new imaging position, e.g., from a position for a CC mammogram to a position for an MLO mammogram. In the case of the Selenia Dimension™ and Gemini™ fused tomosynthesis/mammography breast imaging systems, source support arm 14 and x-ray receptor arm 18 can be locked together to rotate in the same manner as the C-arm in the Selenia™ system, or can be unlocked so that one or both can rotate separately about rotation axis 12 at rates and through angles relative to the breast and each other as needed for tomosynthesis imaging. In addition, image receptor 22 can rock, e.g., about an axis passing through its imaging surface, relative to breast support 20 while the first arm 14 rotates about axis 12 in the course of taking a series of tomosynthesis projection images. Arm 14 can rotate through an angle different from the angle through which receptor 22 rocks in the course of taking a series of tomosynthesis images.

In a typical breast imaging procedure in which x-ray source 16 and breast platform 20 are aligned vertically, whether for mammography or tomosynthesis, a technician retracts patient shield 28 to an access position that is away from the patient's chest and head, to an access position that is closer to the vertical portion (as viewed in FIG. 2) of receptor support arm 18, adjusts the height above the floor of breast platform 20 and moves compression paddle 26 up, for example to its position shown in FIGS. 1 and 2. The patient leans forward such that the breast to be imaged rests on breast platform 20 and the patient's chest wall presses against a forward edge 20a of breast platform 20. At this time, in it access position, patient shield 28 is away from the patient's chest wall and head, which provides the technologist or other health professional convenient access to manually adjust the breast position relative to breast platform 20 while lowering compression paddle 26 and to continue to adjust the breast and perhaps adjacent tissue as needed. After the desired degree of compression is reached, which may be different for mammography compared with tomosynthesis imaging, the technician extends patient shield 28 by moving shield 28 along shield support arm 30 to a protective position seen in FIG. 1 such that the patient's head is in front of or to the side of patient shield 28. After a possible scout shot that helps set AEC parameters, x-ray imaging starts, with patient shield 28 helping to keep the patient's head, arms, shoulders and hands out of the path of the imaging x-ray beam. If conventional screening mammography shots are taken, a CC shot is taken and then the breast is released by moving compression paddle 26 up and possibly also retracting patient shield 28 to the access position, and source support arm 14 and x-ray receptor arm 18 rotate as a unit to a new imaging position such as the MLO position, at which the procedure is repeated. In breast tomosynthesis imaging, while the breast remains immobilized and patient shield 28 remains in its protective position, source support arm 14 moves relative to the immobilized breast possibly but not necessarily also relative to x-ray receptor support arm 18 to allow taking several projection x-ray images from different angles. A conventional mammography image may be taken at one of these angles, at an appropriate higher x-ray dose compared with the dose for a tomosynthesis projection image. Alternatively, x-ray imaging for mammography and/or tomosynthesis may be allowed when patient shield 28 is in its access position.

As seen in the schematic view of FIG. 3, patient shield 28 moves toward and away from the patient's chest and head (moves left and right in the view of FIG. 3) relative to x-ray source 16 and x-ray imaging receptor 22 to thereby move patient shield 28 between the protective position seen in FIGS. 1 and 3, and the access position seen in FIG. 2. Although a particular access position is shown in FIG. 2, it should be understood that for the purposes of this invention the access position can be any position that is away from the protective position and facilitates access to the patient's breast while compressing the breast. Preferably, the access position also allows taking x-ray images with patient shield 28 and its support mechanism being out of the imaging beam. The system may be provided with interlocks (see FIGS. 4a, 4b and 5) to allow x-ray imaging exposure only when shield 28 is in its protective, or only in its access position, or in both, but not at intermediate positions. Similarly, the system may be provided with interlocks to allow x-ray imaging only when shield 28 is not detected in the intermediate zone between its access and protective positions. In a still further embodiment, the system can be set to allow x-ray imaging exposure only when patient shield 28 is in its protective position. The technologist can move patient shield 28 manually between its protective and access positions, or motorized movement may be provided.

Figure 4A:
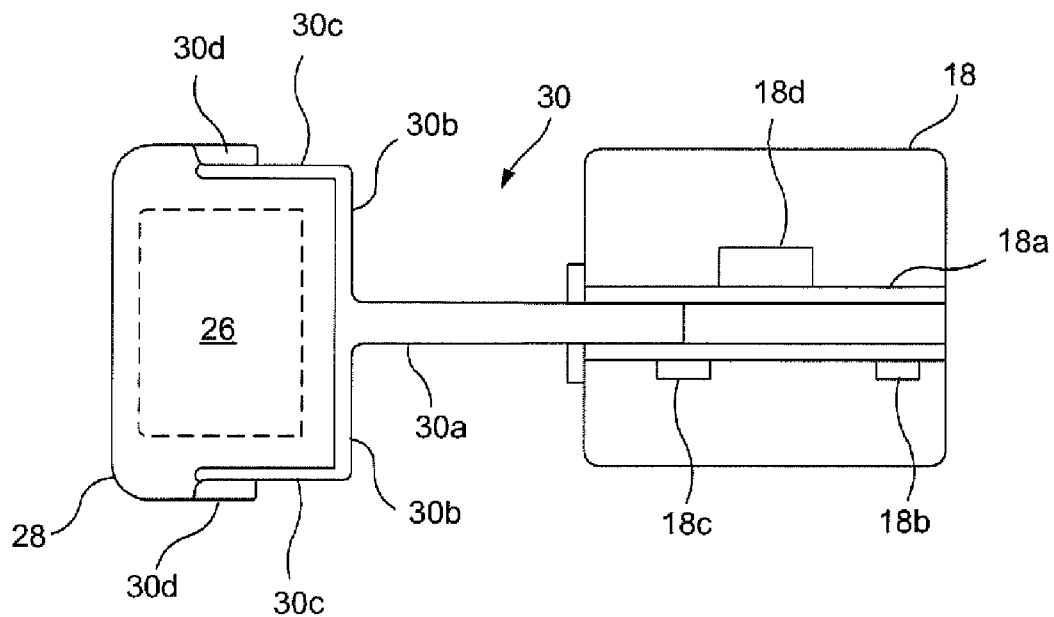
FIGS. 4a and 4b are top plan views of two examples of a shield and shield support.

As illustrated in FIG. 4a, which is a top view detail, shield arm 30 may comprise a central bar 30a that is received in receptor support arm 18 and has at its front end two cross-bars 30b ending with respective tines 30c that support patient shield 28 through pads 30d secured to both tines 30c and patient shield 28. The outline of compression paddle 26 is illustrated in dashed lines. When patient shield 28 is in its protective position shown in FIG. 1, patient shield 28 and all portions of shield arm 30 are out of the x-ray beam used for imaging the breast. Similarly, when patient shield 28 is in it access position shown in FIG. 2, patient shield 28 and shield arm 30 preferably are out of the imaging x-ray beam. Central bar 30a is received in a raceway 18a inside receptor support arm 18, which raceway supports bar 30a and allows movement thereof along the length of central bar 30a. An interlock 18b secures patient shield 28 in its access position and provides an access electrical signal that is to the system controls indicating that patient shield 28 is in its access position. An interlock 18c secures patient shield 28 in its protective position and provides a protective electrical signal that is sent to the system controls to indicate that patient shield 28 is in its protective position. A motor 18d can be provided in receptor support arm 18 to motorize the motion of patient shield 28 between its protective and access positions, although motorized motion is not required and manual systems and method of moving patient shield 28 also are envisioned.

Figure 4B:
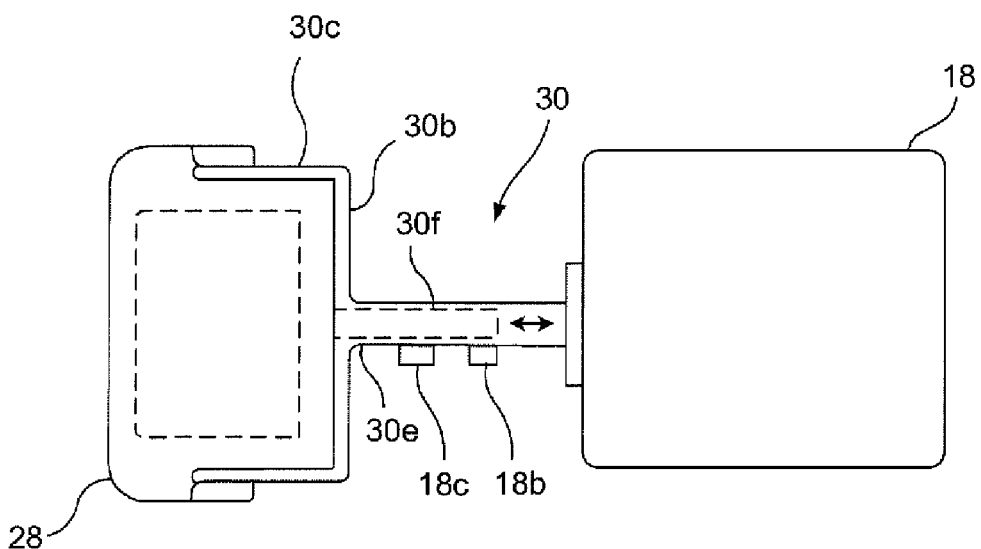

FIG. 4b is otherwise similar to FIG. 4a but shows a first preferred variant in which shield arm 30 comprises a telescoping arrangement of an outer hollow tube 30e enclosing an internal support arm 30f that moves left and right (toward and away from the patient's chest) to place shield 28 in the protective position or the access position. Outer tube 30e is fixedly secured to receptor support arm 18. Interlocks 18b and 18c, shown schematically in FIG. 4b, serve function comparable to their functions in the arrangement of FIG. 4a. Shield 28 in the FIG. 4b configuration can be moved manually between its protective and access positions, or the movement can be motorized through appropriate cabling and/or gearing arrangements and a motor similar to motor 18a (not shown in FIG. 4b) that can be inside tube 30e or inside source support arm 14, for example.

FIGS. 6a, 6b, 7a, 7b and 8 illustrate a second, currently preferred implementation of a mechanism for supporting and moving a shield 30 that has a currently preferred shape. Support 60 comprises a cross-member 60a secured to an arm 60b. Cross-member 60a removably attaches to receptor support arm 18 with prongs 60c fitting within matching openings 18a in arm 18, which are positioned such that arm 60 and shield 28 are just under the horizontally extending portion of source support arm 14 (as viewed in FIG. 1). When attached to arm 18, arm 60 is locked thereto with a manually operated locking mechanism 60d (FIG. 8) but can be unlocked manually so shield 28 and its support arrangement can be removed if desired. A carriage 60 rides underneath arm 60b, along the length thereof, on a rail 60f as further supported by channels 60e. A cross-member 60h is secured to carriage 60e and wings 28a of shield 28 are secured to the lateral ends of cross-member 60h. Buttons 60i, when pressed, move bars 60j against a biasing force to release carriage 60e from being locked in position along arm 60b, so carriage 60e and, with it, shield 28, can be moved between its protective and access positions. When buttons 60i are released, carriage 60i locks in position to arm 60b. The locking of carriage 60e to arm 60b can be by magnetic latches, e.g., at 60k, or another locking mechanism that can be released by pressure on buttons 60i. A sensor, such as at 60m (FIG. 7b), is activated when carriage 60e is adjacent to thereby detect that shield 28 is in its protective position and supply a sensor signal (comparable to that from interlock 18c) to a control computer 32 (FIG. 5) to indicate that shield 28 is in its protective position. Another sensor, such as at 60n (FIG. 6a), is activated when carriage 60e is adjacent to thereby supply a similar sensor signal, comparable to that from interlock 18b, to control computer 32 to indicate that shield 28 is it its access position.

Figure 6A:
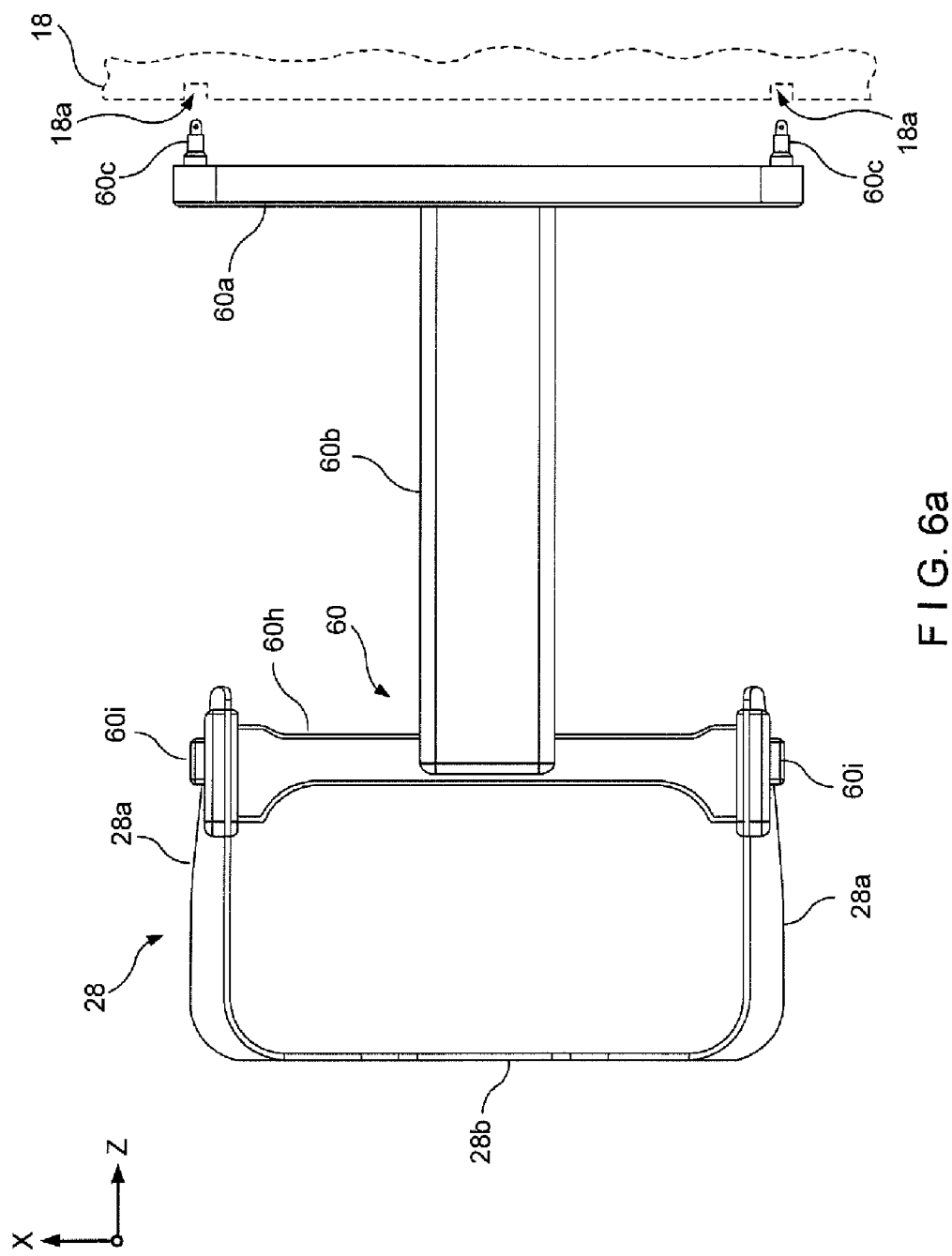
FIGS. 6a and 7a are top views of a preferred implementation of a shield and shield support in the protective and access positions, respectively.
Figure 7A:
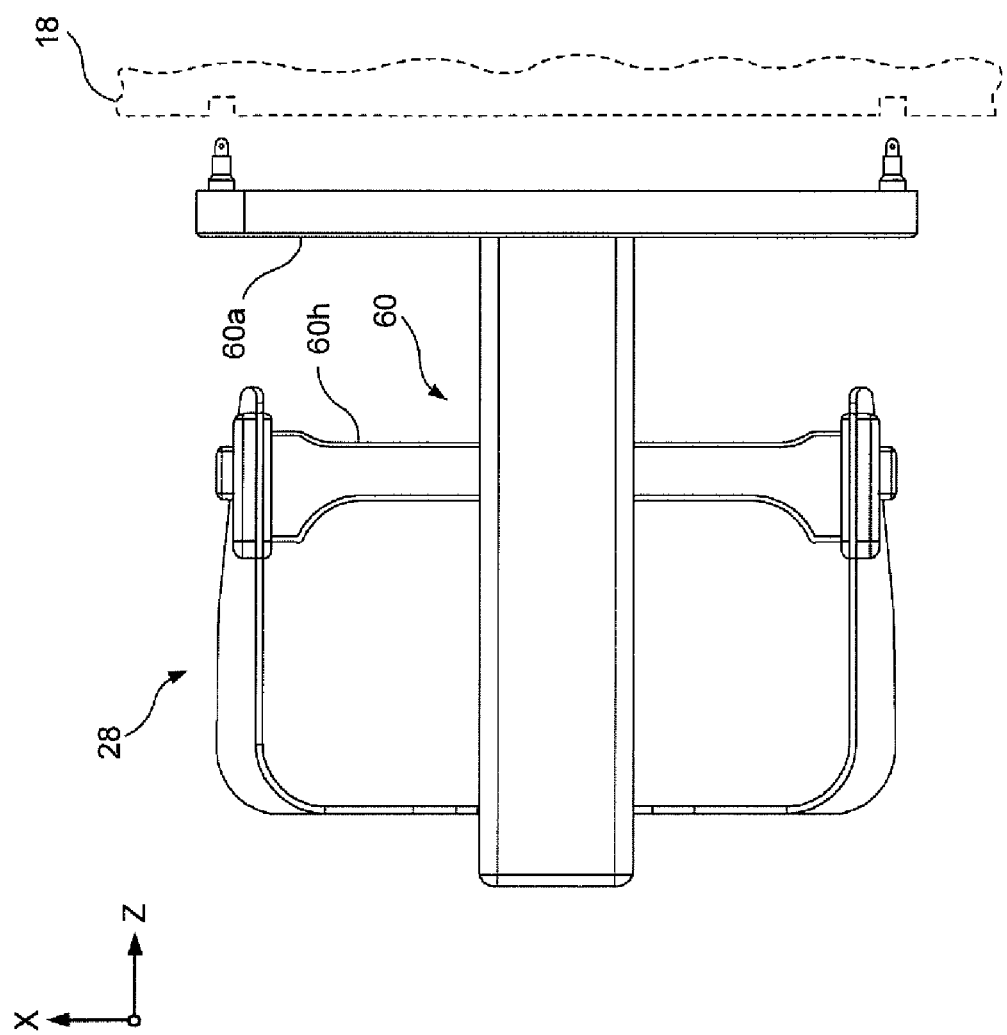
Figure 8:
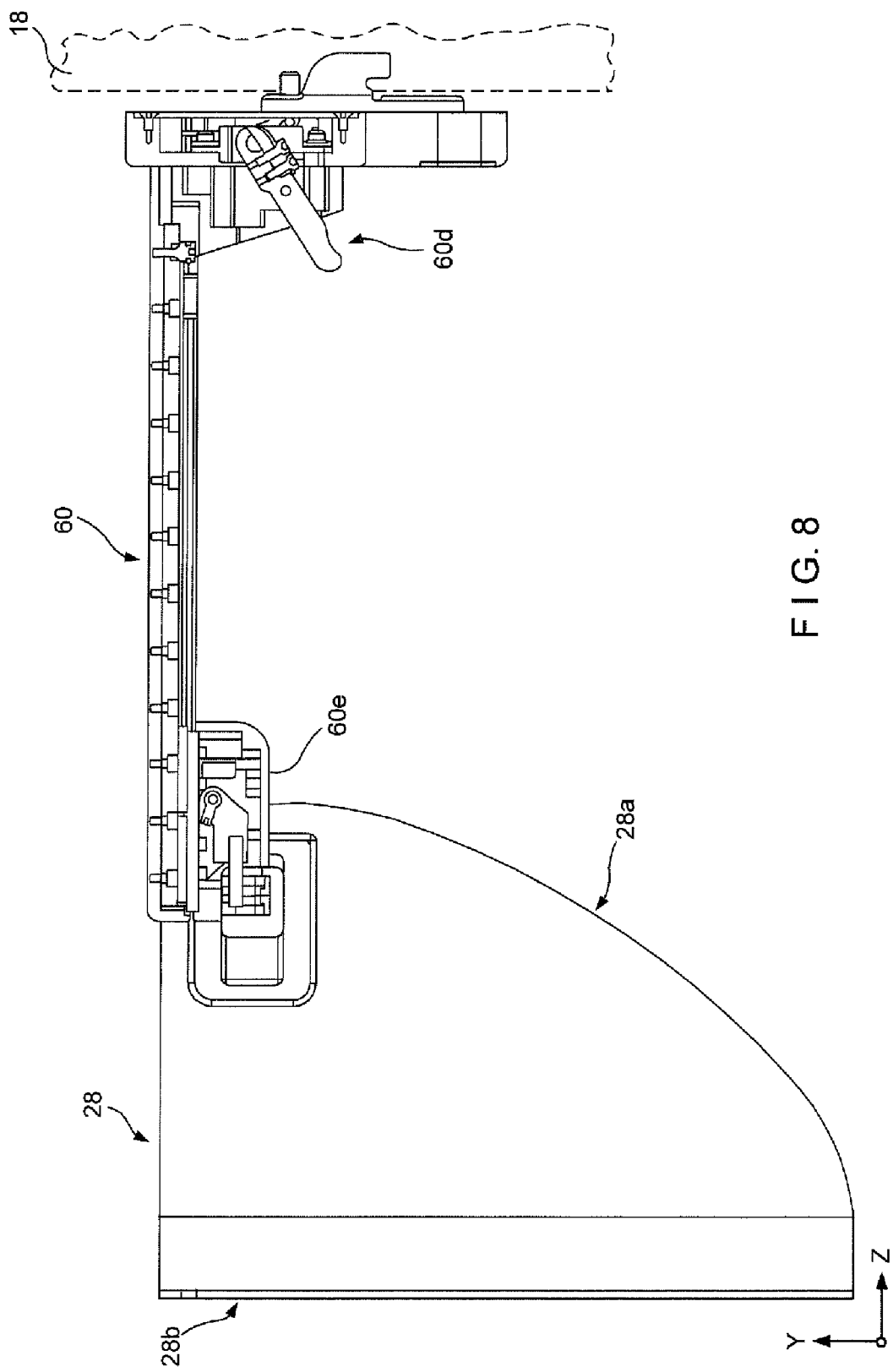

As seen, e.g., in FIGS. 6a, 6b and 8, shield 28 preferably is made of a continuous, transparent or translucent material, bent into a U-shape as viewed in FIGS. 6a and 6b, and comprises wings 28a and a front portion 28b. Preferably, wings 28a have tapered undersides (as viewed in FIG. 8), and preferably the sides of wings 28 bulge out so their top edges, seen in FIG. 6a, are closer to each other than their bottom edges, seen in FIG. 6b. Preferably, all edges of shield 20 are beveled.

Figure 5:
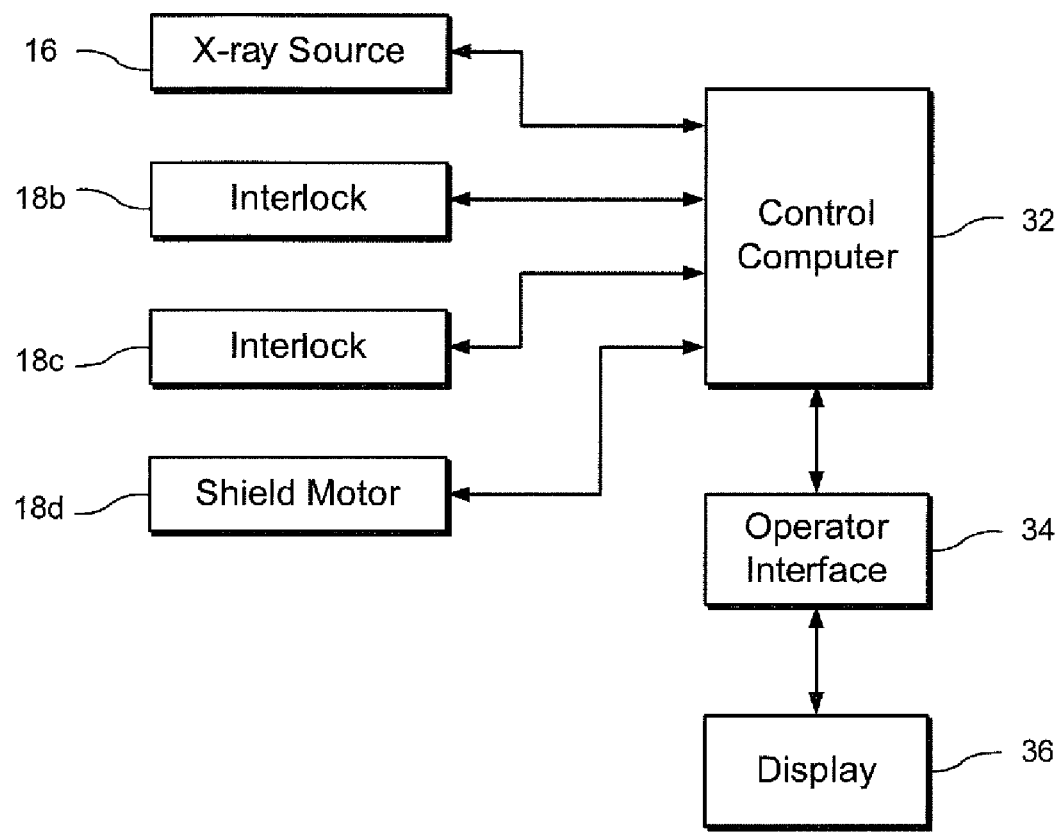
FIG. 5 is a block diagram illustration of controlled shield motion and interlocks.

FIG. 5 is a schematic illustration of system components involved in moving patient shield 28 between its protective and access positions and with coordinating the motion with imaging x-ray exposures. A control computer 32 can be implemented by programming the computer system that is a part of the mammography and/or tomosynthesis system equipped with patient shield 28 to carry out the control operations described herein. An operator interface 34 and a display 36 can be the known subsystems of the mammography/tomosynthesis system equipped with a patient shield 28. Interlocks 18b and 18c (or sensors 60m and 60n) provide control computer 32 with information indicating whether patient shield 28 is in one of its protective and access positions. Control computer 32 can provide this information for display at display 36 for confirmation by the technician. If motorized motion of patient shield 28 is selected, shield motor 18*d* can be enabled by control computer 32, in response to a command entered by the technician at operator interface 34, to move patient shield 28 from one to the other of its protective and access positions. Shield motor 18*d* can be an electric motor moving patient shield 28 through an arrangement such as a rack-and-pinion or a cable configuration, using known technology. In operation, the technician moves patient shield 28 manually or through motor 18*d*, to its access position or confirms that it is in the access position, and positions and adjusts the patient's breast while compressing it between breast platform 20 and compression paddle 26, with the patient's chest pressed against front edge 20*a* of breast platform 20. When ready to take an x-ray image, the technician may take the image with patient shield 28 in its access position but typically the technician will first move patient shield 28 to its protective position, either manually or by entering a command through operator interface 34, which command control computer 32 executes by commanding shield motor 18*d* to move patient shield 28 accordingly. Display 36 can show icons or other information indicating the position of patient shield 28. When the technician is satisfied with the position of the breast and of patient shield 28, the technician may enter appropriate commands at operator interface 34 for the desired type of imaging, such as for a mammogram and/or for tomosynthesis projection images, and control computer 32 proceeds to control the appropriate system components to carry out the imaging. If interlocks 18*b* and 18*c* (or sensors 60*m* and 60*n*) indicate that patient shield 28 is not in one of its protective and access positions, control computer 32 preferably does not allow x-ray source 16 to be energized to emit an x-ray beam. In the alternative, control computer 32 may be configured to allow an x-ray exposure only when interlock 18*c* or sensor 60*m* indicates that 28 is in its protective position. As another alternative, control computer may be configured to also allow an x-ray exposure when interlock 18*b* or sensor 60*n* indicates that shield 28 is in its access position. Other embodiments in which no interlocks are used are also envisioned. In a preferred embodiment one or more of the access position, protective position and length of the face shield are selected to that the face shield does not interfere with the imaging of the patient in either of the access or protective positions.

Another currently preferred implementation, in which a patient shield is mounted both for side-to-side motion and back-and-forth motion relative to x-ray source 16 and x-ray imaging receptor 22, is illustrated in FIGS. 9-14. Referring to the perspective view of FIG. 9, a receptor support arm 90 is otherwise similar to receptor support arm 18, and is similarly mounted to a support column 10 for rotation and vertical motion, but has a concave front face 90*a* to which a bracket 92 is removably mounted. Bracket 92 is mounted to arm 90 in a manner similar to the mounting of arm 60*a*, i.e., using a pair of hooks 92*a* (similar to hooks 60*c*1 in FIG. 8) and pins (not seen in FIG. 9 but similar to pins 60*c*2 in FIG. 8), that fit in matching openings 90*b* in arm 90. A manual locking mechanism 92*c* locks bracket 92 to arm 90 when shield 28 is to be used, and unlocks bracket 92 from arm 90 so the bracket and shield can be removed, if desired, from arm 90 and the x-ray system of which arm 90 is a part.

Figure 9:
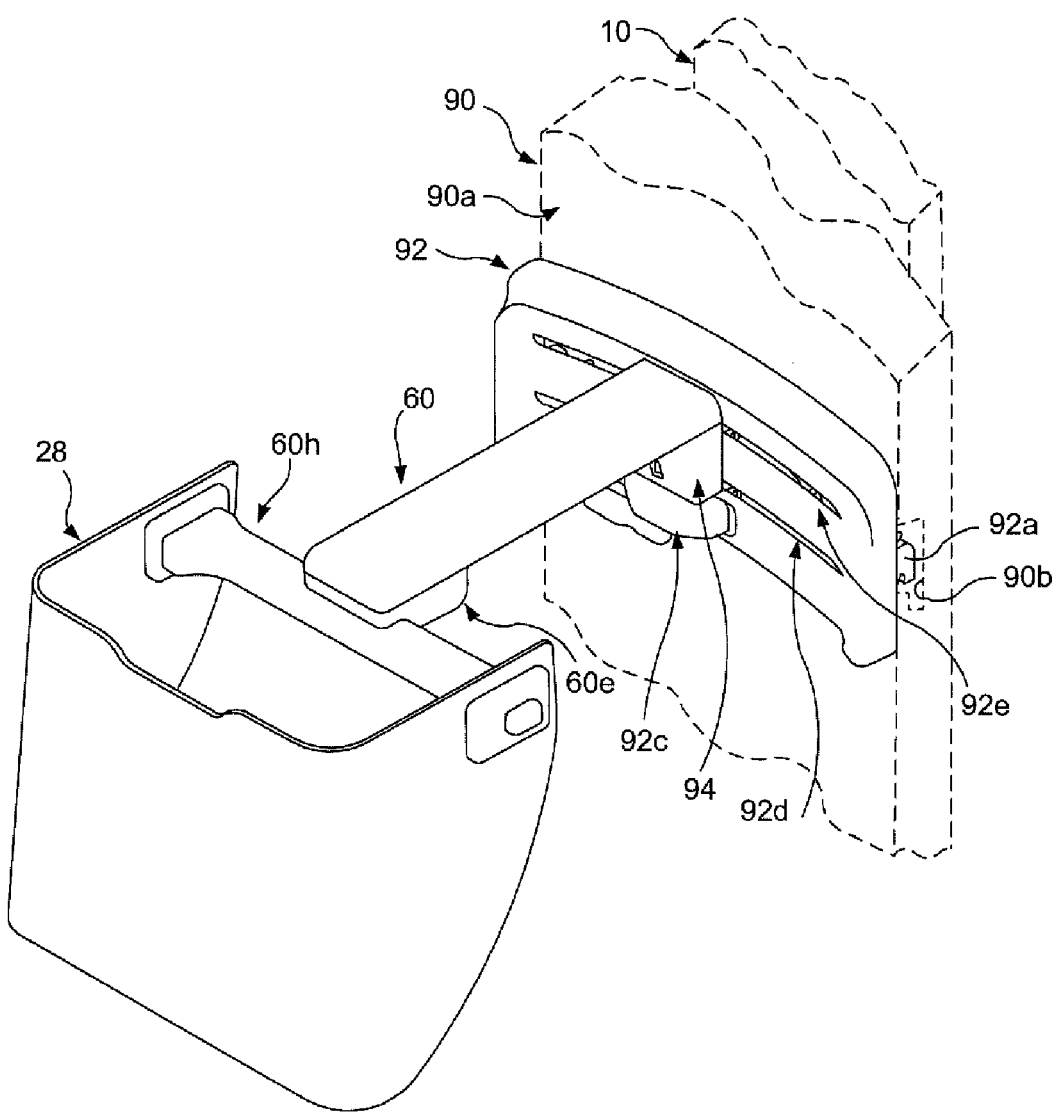
Figure 10:
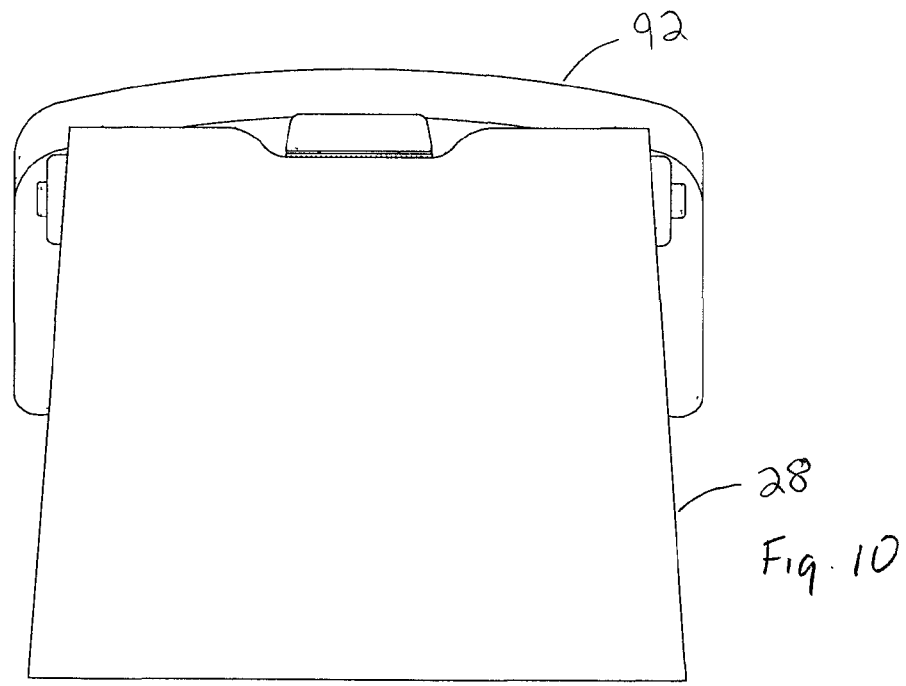
Figure 11:
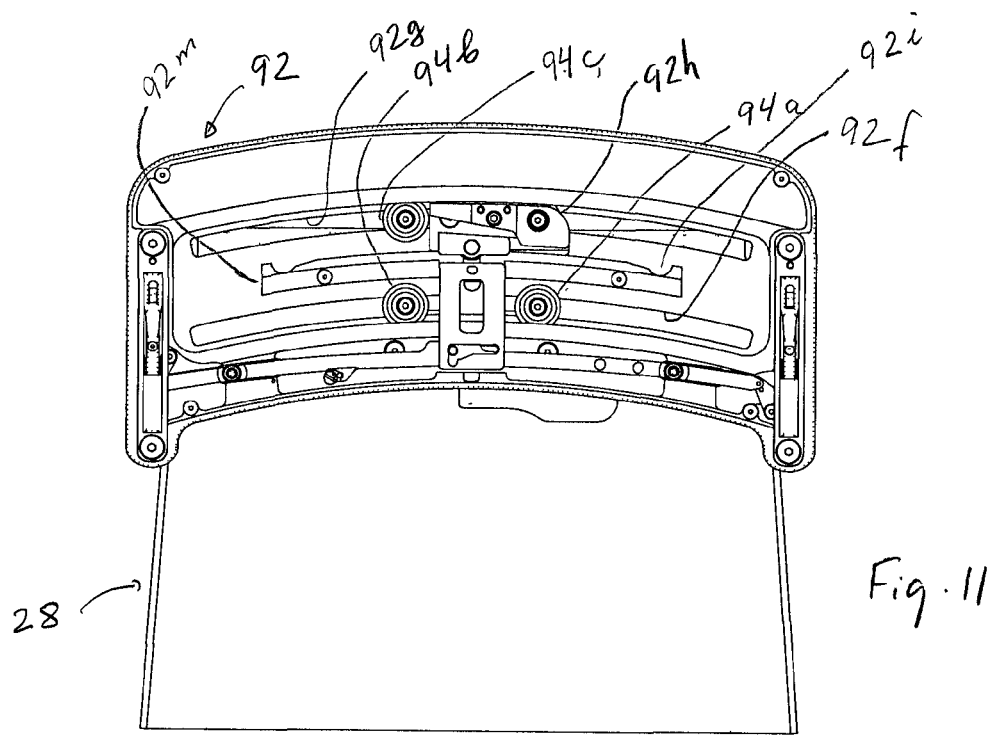
Figure 13:
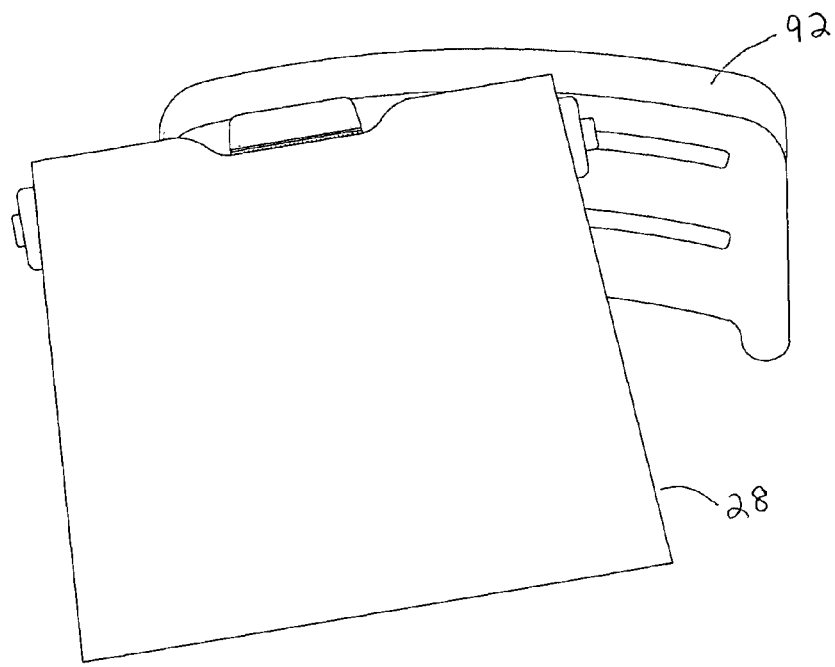
Figure 14:
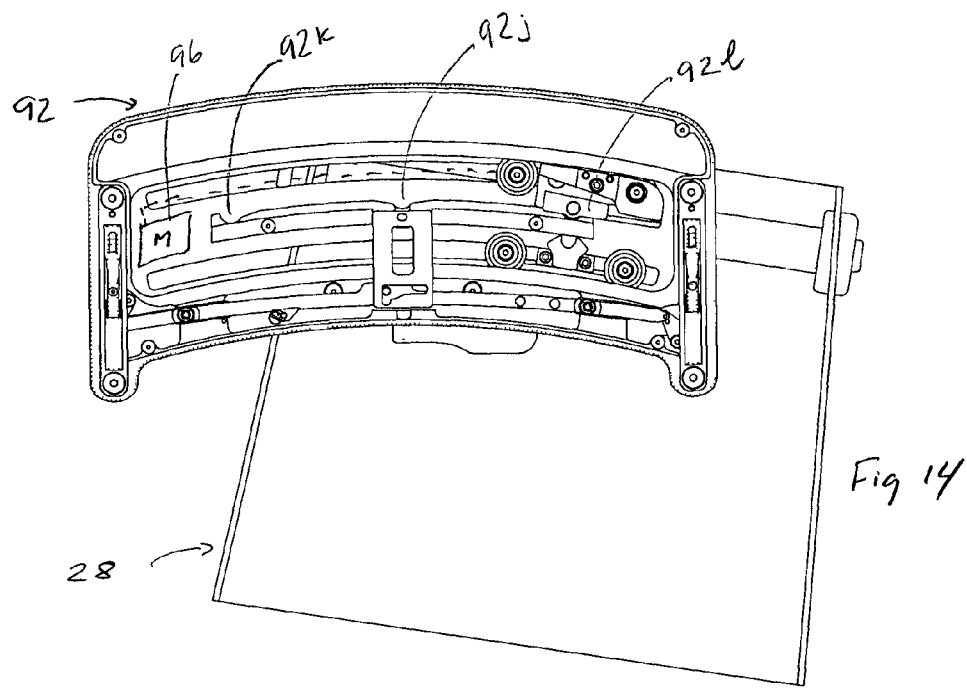

Arm 60 in FIG. 9 is the same as in FIGS. 6*a* through 8, and supports shield 28 for back-and-form movement in the same manner and using the same means as in FIGS. 6*a*-8. However, instead of being attached to cross-member 60*a*, as in FIGS. 6*a*-8, in the implementation of FIG. 9 the back end of arm 60 is mounted for side-to-side movement relative to bracket 92, through an extension 94 secured to the back end of arm 60. Extension 94 has pins (not visible in FIG. 9) that extend into slots and ride within slots 92*c* and 92*d* in bracket 90. Referring to FIGS. 11 and 14, which are elevations as seen from the back of bracket 92 (and omit an illustration of arm 90 and column 10, as do FIGS. 10, 12 and 13), the pins that extend into lower slot 90*d* are secured to lower rollers 94*a* and 94*b* riding over raceway 92*f* of bracket 92 and at least one upper roller 94*c* riding in a downwardly facing raceway 92*g* of bracket 92. A similar upper roller 92*g*, riding in raceway 92*g*, may be provided. As seen in FIGS. 11 and 14, bracket 92 can move laterally, side-to-side in the illustrated views, from the center position seen in FIG. 11 to an left offset position seen in FIG. 14 (and to a right offset position, which is a mirror image of the position seen in FIG. 14). A detent bar 92*m* has detents 92*i*, 92*j* and 92*k* that cooperate with a spring biased detent roller 92*l* serving to retain arm 60 and thus shield 28 in one of the left, center and right positions of its side-to-side movement. While arm 60 can be moved side-to-side relative to bracket 92 manually, as an alternative a motor schematically illustrated at 96 and suitably coupled to extension 94 can be provided for side-to-side motion under the control of computer 32 (FIG. 5). Interlocks or sensors similar to interlocks or sensors 18*b* and 18*c* can be associated with the side-to-side motion of extension 94 to provide control computer 32 with sensor signals indicative of the position of arm 60 and extension 94 in their side-to-side motion relative to bracket 92.

The central position of the side-to-side motion of arm 60 and thus shield 28 is illustrated in perspective in FIG. 9, in front elevation in FIG. 19, and in back elevation in FIG. 11. The left position in arm 60 and shield 28 is illustrated in perspective in FIG. 12, in front elevation in FIG. 13, and in back elevation in FIG. 14. In each of FIGS. 9-12, shield 28 is shown in its protective position, as it is in the example of FIG. 6*a*. It should be understood that the implementation of FIGS. 9-14 additionally includes back-and-forth movement of shield 28, between its protective position seen in FIG. 6*a* and its access position seen in FIG. 7*a*, so that the health professional using the system can select between several modes of x-ray imaging: (1) imaging the patient's breast with shield 28 in its protective position and in one of its center, left and right positions; (2) imaging the patient's breast with shield 28 in its access position and in one of its center, left and right positions; (3) imaging the patient's breast with the bracket 92 (and shield 28) removed from the imaging system. Similarly, the health professional can manually adjust the patient's breast during compression before imaging in any one of the aforesaid side-to-side and back-and-forth positions of arm 60 and shield 28. As in the protective and access positions in the implementations of FIGS. 1-8, in the implementation of FIGS. 9-14 shield 28 and all elements associated therewith preferably are out of the imaging x-ray beam when in the protective and access positions of the back-and-forth motion of shield 28 and in the left, center and right position of the side-to-side movement of shield 28.

In typical use of an x-ray breast imaging system with a patient shield of the type illustrated in FIGS. 9-14, the patient leans forward with her chest wall against the front end 20*a* of breast platform 20 and with a breast resting on platform 20. The health professional slowly brings down compression paddle 26 while adjusting the patient's breast for purposes such as to make the compressed breast as uniform in thickness and practical and to ensure that tissue of interest would be within the imaging x-ray beam. After the desired degree of breast compression and immobilization has been reached, the health professional may confirm various settings of the imaging system and may take a low-dose pre-exposure for data useful in setting imaging parameter, may set or confirm system settings such as technique factors and position of system elements (including shield 28), and command the taking of one or more imaging x-ray exposures while the breast remains compressed and immobilized. In this process, the health professional may move face shield 28 between its side-to-side and back-and-forth positions as needed or desired, of may work with the face shield entirely removed from the imaging system. In the example of using the x-ray imaging system for a mammography image in the CC imaging position, in which breast platform 20 and source support arm 14 are in the positions seen in FIGS. 1 and 2, the health professional may leave shield 28 in its center position seen in FIG. 9 but with shield 28 in its access position seen in FIG. 7a while compressing and adjusting the patient's breast, and move shield 28 to its protective position seen in FIG. 6a before taking an imaging x-ray exposure. In the example of taking a mammography image in another orientation, such the MLO orientation, the health professional first rotates the source support arm 14 and the receptor support arm 18 about axis 12 (or about respective different axes), so that breast platform 20 is no longer horizontal, and the remainder of the process is the same as for the CC position. In the example of using the imaging system for tomosynthesis images while breast platform 20 is in the position seen in FIGS. 1 and 2, the procedure may be the same, except that after the breast is compressed the source support arm 14 rotates relative to receptor support arm 18 while a succession of tomosynthesis projection x-ray images are taken. Alternatively, for obtaining the same tomosynthesis projection image, the health professional may move shield 28 to one of its left and right position before taking the tomosynthesis projection images. In the example of taking tomosynthesis images while breast platform 20 is not horizontal, first arms 14 and 18 are rotated, and then the tomosynthesis procedure is the same. The implementations illustrated in FIGS. 1-8 typically are used similarly, except for the lack therein of side-to-side movement of shield 28.

As explained in commonly owned U.S. Pat. No. 7,245,694, it may be desirable to take tomosynthesis projection images while the x-ray source is moving through a trajectory that is asymmetrical with respect to a normal to the imaging plane of the x-ray image receptor. In that case, an imaging system that has the shield arrangement illustrated in FIGS. 9-14 typically would be used with shield 28 in one of its left and right positions, e.g., as illustrated for shield 300 in FIGS. 13 and 14, respectively, of said patent, in addition to using, if desired, the back-and-forth motion of shield 28, between its protective and access positions.

The description above assumes that the system starts in an orientation suitable for a CC image, but it should be understood that the system operates similarly when the starting position is suitable for another orientation such as for an MLO image. Indeed, the motion of patient shield 28 between its two position can be more helpful when the starting position had x-ray source 16 and x-ray imaging receptor 22 aligned along a non-vertical line, because such alignment may make access by the technician more difficult.

Thus, a system and a method are disclosed describing a patient shield that moves toward and away from the patient's chest between an access position that facilitates the technologist's access to the breast during compression, and a protective position. In addition, the system may allow an x-ray tube to rotate about an immobilized patient breast relative to the shield, in which the shield protects the patient from moving system components.

The invention claimed is:

1. An x-ray system for imaging a patient's breast, comprising:
an x-ray source selectively emitting an imaging x-ray beam, an x-ray imaging receptor receiving the imaging beam, and a breast platform between the source and the receptor, said breast platform having a front edge against which a patient's chest wall presses when the patient's breast is imaged with said imaging beam;
a patient shield and a shield support supporting the shield between the source and the breast platform at least for selective back-and-forth movement of the shield between selected back-and-forth positions comprising a protective position and an access position;
wherein the protective position is closer to the front edge of the breast platform than the access position.

2. A system as in claim 1 in which said shield support additionally supports the shield for side-to-side movement relative to the source and the breast platform between selected side-to-side positions.

3. A system as in claim 2 further including sensors sensing whether the shield is in at least one of said selected back-and-forth and side-to-side positions and providing sensor signals indicative thereof.

4. A system as in claim 3 further including a control computer coupled to the sensors and the source and configured to control said source according to said sensor signals.

5. A system as in claim 4 in which said control computer is configured to control the source to prevent emission of said imaging beam when the shield is between the source and receptor but not in at least one of the selected back-and-forth positions.

6. A system as in claim 4 in which said selected side-to-side positions include a left position, a right positions and a center position and said control computer is configured to control the source to prevent emission of said imaging beam when the shield is between the source and receptor but not in at least one of the left, right and center positions thereof.

7. A system as in claim 4 further including a display coupled to said control computer and displaying an indication of the selected position of said shield, and an operator interface coupled to the control computer to receive and convey to the control computer an operator's confirmation that the shield is in a position in which the source should emit the imaging beam.

8. A system as in claim 4 further including a shield drive motor coupled to the shield and to the control computer and selectively driving the shield between at least two of said selected positions thereof in response to commands from the control computer.

9. A system as in claim 2 further including locks releasably locking the shield in at least one of the selected positions, said locks being manually releasable to thereby unlock the shield for manually moving the shield between said at least two selected positions.

10. A system as in claim 1 further including sensors sensing whether the shield is in at least one of said selected back-and-forth positions and providing sensor signals indicative thereof.

11. A system as in claim 10 further including a control computer coupled to the sensors and the source and configured to control said source according to said sensor signals.

12. A system as in claim 11 in which said control computer is configured to control the source to prevent emission of said imaging beam when the shield is between the source and receptor but not in at least one of the selected back-and-forth positions.

13. A system as in claim 12 further including a display coupled to said control computer and displaying an indication of the selected position of said shield, and an operator interface coupled to the control computer to receive and convey to the control computer an operator's confirmation that the shield is in a position in which the source should emit the imaging beam.

14. A system as in claim 12 further including a shield drive motor coupled to the shield and to the control computer and selectively driving the shield between at least two of said selected positions thereof in response to commands from the control computer.

15. A system as in claim 1 further including locks releasably locking the shield in at least one of the selected positions, said locks being manually releasable to thereby unlock the shield for manually moving the shield between said at least two selected positions.

16. A system as in claim 1 in which said shield is generally U-shaped in a section transverse to the imaging beam and comprises a front portion and a pair of wings, said wings having upper edges closer to the source and lower edges closer to the receptor, and said shield flaring such that the upper edges are closer to each other than the lower edges.

17. A system as in claim 1 operative selectively in a mammography mode and in a tomosynthesis mode and including a first support supporting the source, a second support supporting the receptor, breast platform and the shield support, said first and second arms being mounted for rotation in a first mode in which they are locked to each other and rotate as a unit and in a second mode in which they are unlocked from each other so that at least one can rotate relative to the other.

18. A method of operating a breast imaging x-ray system, comprising:
positioning a patient's breast on a breast platform having a front edge against which the patient's chest wall presses;
operating a patient shield supported at least for back-and-forth movement relative to the breast platform between selected back-and-forth positions relative to the breast support, including a protective position and an access position, by moving the patient shield toward the front edge of the breast platform and into the protective position from the access position in which the shield is further from the breast platform's front edge; and
taking at least one x-ray imaging exposure of the breast with an imaging x-ray imaging beam emitted from an x-ray source on one side of the breast and the breast platform and received by an x-ray imaging receptor on the other side, while the patient shield is in its protective position and the beast remains compressed.

19. A method as in claim 18 wherein said patient shield is further supported for side-to-side movement relative to the breast platform between selected side-to-side positions, and further operating the patient shield, before taking said at least one imaging exposure, to move the patient shield side-to-side relative to the breast platform to a selected one of side-to-side positions.

20. A method as in claim 19 including providing sensors and using the sensors to sense whether the shield is in at least one of its selected positions and emit sensor signals indicative thereof.

21. A method as in claim 20 including providing a control computer coupled to the sensors and the source and using the control computer to control said source according to said sensor signals.

22. A method as in claim 21 including using the control computer to control the source to prevent emission of said imaging beam when the shield is between the source and receptor but not in at least one of the protective and access positions.

23. A method as in claim 21 including providing a display coupled to said control computer and displaying an indication of the position of said shield, providing an operator interface coupled to the control computer to receive and convey to the control computer an operator's confirmation that the shield is in a position in which the source should emit the imaging beam.

24. A method as in claim 21 including driving the shield with a drive motor coupled to the shield and to the control computer and selectively driving the shield between at least two of the selected positions thereof in response to commands from the control computer.

25. A method as in claim 19 including releasably locking the shield in at least one of its selected positions, and manually releasing the locks to manually move the shield from one to another of the selected positions thereof.

26. A method as in claim 19 including selectively operating in a mammography mode in which a first support supporting the source and a second support supporting the receptor, breast platform and the shield support are mounted for rotation as a unit and in a tomosynthesis mode in which the first and second support arms are unlocked from each other so that at least one rotates relative to the other.

27. A fused tomosynthesis/mammography system for imaging a patient's breast with x-rays, comprising:
an x-ray source selectively emitting an x-ray imaging beam, an x-ray imaging receptor receiving the imaging beam, and a breast immobilizer between the source and receptor, said breast immobilizer being in the path of the imaging beam and having a front edge against which the patient's chest wall presses when a patient's breast is being imaged with said imaging beam;
a first support arm supporting the source and mounted for rotation about a first axis spaced from the source;
a second support arm supporting the breast immobilizer and the receptor and mounted for rotation about a second axis;
a control computer selectively rotating the first and second support arms and the breast immobilizer as a unit in a mammography mode of operation of the system and, in a tomosynthesis mode of operation, rotating at least the first support arm relative to the breast immobilizer;
a patient shield mounted to said second arm at least for selective back-and-forth motion selected positions comprising a protective position in which the shield is closer to said front edge of the breast immobilizer and an access position in which the shield is further from said front edge.

28. A system as in claim 27 in which said receptor is mounted for rocking motion relative to said breast immobilizer in said second mode of operation.

29. A system as in claim 28 in which in said tomosynthesis mode of operation the source rotates through a first angle and the receptor rocks through a second angle that is different from said first angle.

30. A system as in claim 27 in which said shield is further mounted for selective side-to-side motion relative to said second support arm.

* * * * *